(12) United States Patent  (10) Patent No.: US 9,375,346 B1
Sundheimer et al.  (45) Date of Patent: Jun. 28, 2016

(54) ABSORBENT PADS AND RELATED METHODS

(75) Inventors: Craig Sundheimer, Carlsbad, CA (US); Lloyd Jarvis, Huntington Beach, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 599 days.

(21) Appl. No.: 13/274,200

(22) Filed: Oct. 14, 2011

Related U.S. Application Data

(60) Provisional application No. 61/392,942, filed on Oct. 14, 2010.

(51) Int. Cl.
*A61F 7/00* (2006.01)
*A61F 7/02* (2006.01)

(52) U.S. Cl.
CPC ........... *A61F 7/02* (2013.01); *A61F 2007/0231* (2013.01)

(58) Field of Classification Search
CPC ..... A61F 7/00; A61F 7/02; A61F 2007/0001; A61F 2013/00187; A61F 7/0241; A61F 2007/0214; A61F 2007/0225; A61F 2007/0228; A61F 2007/0231; A61F 2007/0242
USPC .................................. 604/290, 291, 304, 308
See application file for complete search history.

(56) References Cited

U.S. PATENT DOCUMENTS

| | | | | |
|---|---|---|---|---|
| 4,534,354 A | * | 8/1985 | Bonner et al. | 607/108 |
| 4,897,297 A | * | 1/1990 | Zafiroglu | 428/102 |
| 6,162,960 A | | 12/2000 | Klein | |
| 6,576,004 B2 | * | 6/2003 | Johnston | 607/114 |
| 6,849,775 B2 | | 2/2005 | Klein | |
| 7,048,976 B2 | * | 5/2006 | Caceres et al. | 428/34.7 |
| 2005/0118383 A1 | * | 6/2005 | Cargill et al. | 428/68 |
| 2007/0106356 A1 | * | 5/2007 | Carstens | A41D 13/005 607/112 |
| 2009/0299258 A1 | | 12/2009 | Cureington-Sims | |
| 2012/0157904 A1 | * | 6/2012 | Stein | 602/43 |

OTHER PUBLICATIONS

U.S. Appl. No. 14/666,194, filed Mar. 23, 2015, Sundheimer et al.

* cited by examiner

*Primary Examiner* — Lynne Anderson
(74) *Attorney, Agent, or Firm* — Stoel Rives LLP

(57) ABSTRACT

An absorbent pad. A first side of the absorbent pad is configured to abut a patient at a fluid discharging area or other location. Discharging fluid passes through a fluid-permeable liner of the absorbent pad into absorbent material. Liquid may be placed in the absorbent material prior to placing it on a patient and heated or cooled. An overwrap may be wrapped around the patient to hold the hot or cold compress in place while absorbing discharging fluid from the patient. A fluid barrier at a second side of the absorbent pad, parallel with the first side, prevents liquid from passing out of the absorbent pad at the second side. A coupler having hooks is disposed on the second side of the absorbent pad and is configured to engage with fibers of the overwrap in order to secure the absorbent pad in place with respect to the patient and overwrap.

21 Claims, 2 Drawing Sheets

ABSORBENT PADS AND RELATED METHODS

CROSS REFERENCE TO RELATED APPLICATIONS

This document claims the benefit of the filing date of U.S. Provisional Patent Application 61/392,942, entitled "Dressing Systems, Fluid Management Systems, Hot/Cold Pack Systems and Related Methods" to Craig Sundheimer and Lloyd Jarvis which was filed on Oct. 14, 2010, the disclosure of which is hereby incorporated entirely herein by reference.

BACKGROUND

1. Technical Field

Aspects of this document relate generally to articles and devices used in hot and cold compression and articles and devices used to absorb fluids. More specific implementations involve articles and devices used to absorb fluids from humans and animals.

2. Background Art

In various industries and instances there are fluids, such as biofluids, that need to be absorbed or cleaned from a surface including, by non-limiting example, from a floor or from the body of a person or animal. In addition various devices and structures have been devised to apply pressure to a surface such as, by non-limiting example, to the body of a person or animal, while also exposing the surface to a higher or colder temperature. The combination of pressure and temperature treatment is often used when treating injuries.

SUMMARY

Implementations of absorbent pads may include: a first side and a second side substantially parallel with the first side, the first side having a fluid-permeable liner and the second side having a fluid barrier; the first side and the second side at least partially forming a cavity and the first side configured to abut a fluid discharge area of a patient; an absorbent material disposed at least partially within the cavity; and a coupler coupled to the second side and having hooks extending from the second side in a direction substantially away from the first side, wherein the hooks are configured to releasably engage with fibers included in an overwrap used to releasably secure the absorbent pad to the fluid discharge area of the patient at a desired location on the overwrap.

Implementations of absorbent pads may include one, all, or any of the following:

The absorbent material may include an absorbent polymer.

The absorbent pad may have an adhesive on the fluid-permeable liner of the first side configured to adhere the fluid-permeable liner to the fluid discharge area of the patient.

The absorbent pad may be flexible and configured to conform to a contour of the fluid discharge area of the patient.

The absorbent pad may have an antimicrobial agent.

The absorbent material may be configured to assist in the conversion of biofluids from a liquid state to a solid state.

Implementations of an absorbent pad and overwrap may include: a first side and a second side substantially parallel with the first side, the first side having a fluid-permeable liner and the second side having a fluid barrier; the first side and the second side at least partially forming a cavity and the first side configured to abut a fluid discharge area of a patient; an absorbent material disposed at least partially within the cavity; a coupler coupled to the second side and having hooks extending from the second side in a direction substantially away from the first side; and an overwrap having fibers configured to releasably engage the hooks, wherein the hooks and fibers, when engaged together, form a hook-and-loop fastener adapted to hold the absorbent pad to the fluid discharge area of the patient at a desired location on the overwrap; wherein the absorbent material of the absorbent pad can absorb up to about 15 times its weight of 0.9% normal saline solution and up to about 30 times its weight of water.

Implementations of an absorbent pad and overwrap may include one, all, or any of the following:

The absorbent material may be an absorbent polymer.

The absorbent pad and overwrap may include an adhesive on the fluid-permeable liner configured to adhere the fluid-permeable liner to the fluid discharge area of the patient.

The absorbent pad may be flexible and configured to conform to a contour of the fluid discharge area of the patient.

The absorbent pad may include an antimicrobial agent.

The absorbent material may be configured to assist in the conversion of biofluids from a liquid state to a solid state.

Implementations of a method of using an absorbent pad may include: absorbing a predetermined quantity of liquid into an absorbent pad having a fluid-permeable liner in a first side of the absorbent pad, the absorbent pad having an absorbent material configured to absorb a maximum quantity of liquid greater than the predetermined quantity of liquid and further including a second side substantially parallel with the first side; one of heating and cooling the predetermined quantity of liquid in the absorbent material to a desired temperature; and abutting the first side of the absorbent pad to a desired location of a patient.

Implementations of a method of using an absorbent pad may include one, all or any of the following:

The method may include preventing liquid from passing through the second side of the absorbent pad with a fluid barrier.

The method may include securing the absorbent pad to the desired location through the engagement of hooks on the second side with fibers in an overwrap wrapped around the patient at the desired location.

The method may include heating the predetermined quantity of liquid to the desired temperature by microwaving the absorbent pad.

The method may include cooling the predetermined quantity of liquid to the desired temperature by placing the absorbent pad in a refrigerator or freezer.

The method may include inhibiting microbial growth proximate the desired location with an antimicrobial agent dispersed in the absorbent material.

The method may include retaining the absorbed predetermined quantity of liquid within the absorbent pad while absorbing additional liquid from a fluid discharge area of the patient.

The method may include maintaining a substantially dry surface at the fluid-permeable liner after absorbing liquid from a fluid discharge area of a patient by drawing the liquid from the fluid discharge area of the patient into the absorbent material away from the fluid-permeable liner.

The method may include the absorbent material absorbing up to about 15 times its weight of 0.9% normal saline solution.

The method may include the absorbent material absorbing up to about 30 times its weight of water.

Implementations of a method of using an absorbent pad may include: providing an absorbent pad having a fluid-permeable liner in a first side of the absorbent pad and a fluid barrier in a second side of the absorbent pad, the absorbent pad having an absorbent material configured to absorb a predetermined quantity of liquid, the predetermined quantity being one of 0.5 cups, 0.75 cups, 1 cup, and 1.5 cups, the predetermined quantity of liquid being less than a maximum quantity of liquid absorbable by the absorbent material; wherein the absorbent pad is further configured to: allow heating and cooling of the predetermined quantity of liquid in the absorbent material to a desired temperature; and allow the first side of the absorbent pad to contact a desired location of a patient.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

Figure 1:
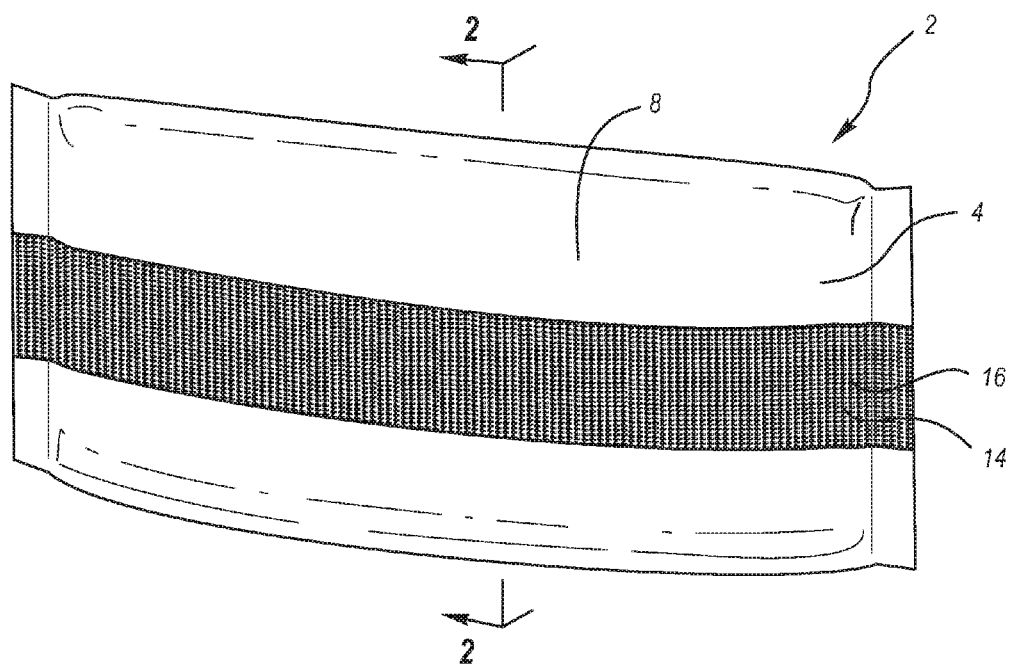
FIG. 1 is a top view of an implementation of an absorbent pad.

This disclosure, its aspects and implementations, are not limited to the specific components or assembly procedures disclosed herein. Many additional components and assembly procedures known in the art consistent with the intended absorbent pads and related methods and/or assembly procedures for an absorbent pad will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such absorbent pads and related methods and implementing components, consistent with the intended operation.

Referring now to FIGS. 1-4, in implementations absorbent pads 2 and 20 include a first side 6 and a second side 8 substantially parallel with the first side 6. The first side 6 and second side 8 at least partially form a cavity 10. In the implementations shown the cavity 10 is fully enclosed within the fluid-permeable liner 4 though in other implementations it may not be fully enclosed within the fluid-permeable liner 4. An absorbent material 12 is disposed at least partially within the cavity 10. In the implementations shown the absorbent material 12 is disposed fully within the cavity 10.

Figure 2:
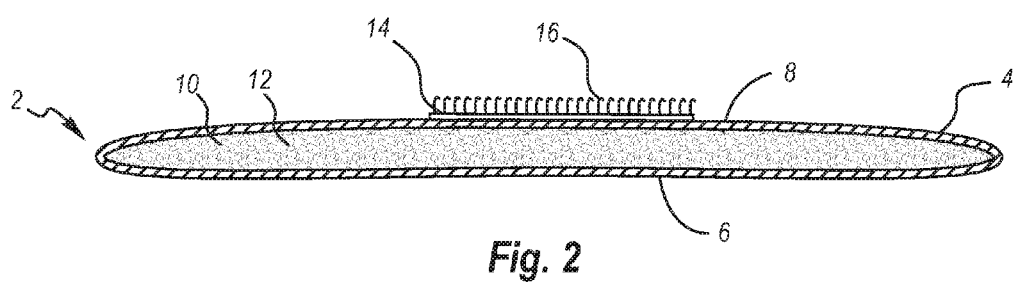
FIG. 2 is a cutaway view of the absorbent pad of FIG. 1 taken along line 2-2.
Figure 3:
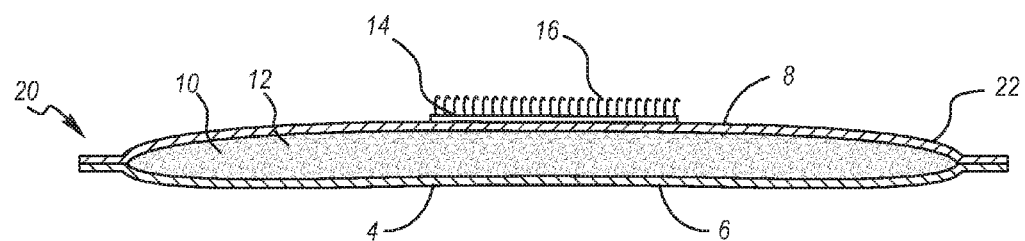
FIG. 3 is a cutaway view of another implementation of an absorbent pad.
Figure 4:
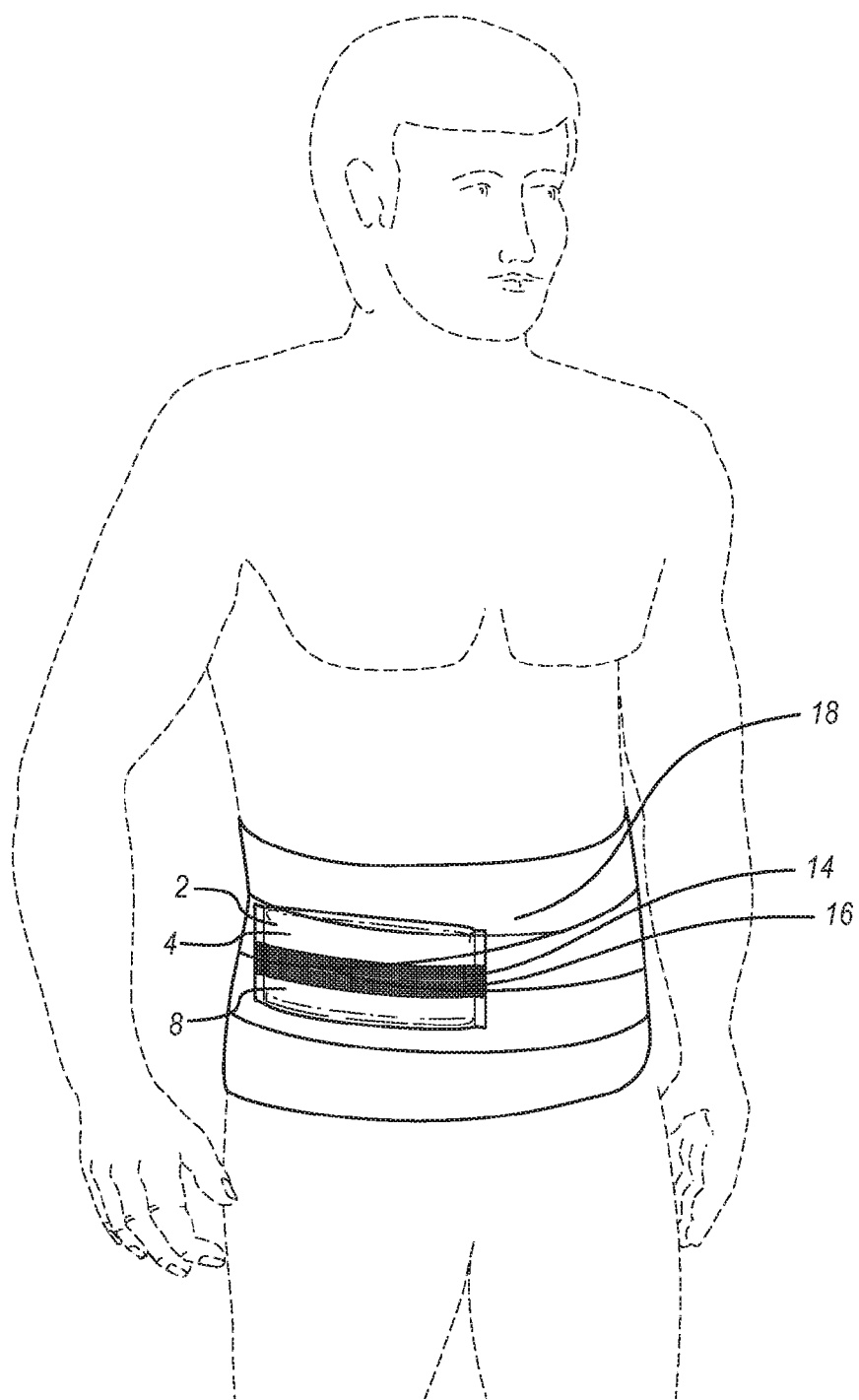
FIG. 4 is a front see-through view of an implementation of an overwrap used on a patient with an absorbent pad.

The fluid-permeable liner 4 is configured to abut a fluid discharge area of a patient, whether human or animal. In the implementations of FIGS. 1-2 and FIG. 4 the fluid-permeable liner 4 forms the first side 6 and second side 8 of an absorbent pad 2. In the implementation of FIG. 3 the fluid-permeable liner 4 forms only the first side 6 of an absorbent pad 20, with the second side 8 being formed by a fluid barrier 22, and the fluid barrier 22 and fluid-permeable liner 4 are joined together at their outer edges. This joining may be accomplished, by non-limiting example, by an adhesive, melting, stitching, gluing, and the like.

In implementations absorbent pads 2 and 20 have a coupler 14 coupled to the second side 8. In the implementation illustrated in FIGS. 1-4, the coupler 14 has hooks 16 which extend outwardly from the second side 8 in a direction away from the first side 6. In other implementations, however, the coupler 14 may be formed from any other structure adapted to releasably or removably engage with or couple with the material of an overwrap 18.

Referring now to FIG. 4, while in use the absorbent pad 2 may be placed proximate a fluid discharge area or another desired location of a patient with the first side 6 facing the fluid discharge area or other desired location on the patient's body. The second side 8 and the hooks 16 of the coupler 14 then face away from the fluid discharge area. An overwrap 18 may then be wrapped around the patient proximate the fluid discharge area or other desired location. The hooks 16 engage with fibers included in the material of the overwrap 18 to secure the absorbent pad 2 in place with respect to the patient and the overwrap 18. In implementations the hooks 16 when engaged with the fibers of the overwrap 18 together form a hook-and-loop fastener. This behavior may be observed particularly in implementations where the overwrap 18 is composed of a fabric or other woven material, such as an ACE™ bandage. In various implementations the fibers need not form or be composed of closed loops but may still function to allow the hooks 16 to engage with the fibers to secure the absorbent pad 2 in place. When an absorbent pad 2 is used the portion of the fluid-permeable liner 4 that forms the first side 6 faces towards the patient and the portion of the fluid-permeable liner 4 that forms the second side 8 faces away from the patient. In implementations wherein an absorbent pad 20 like that illustrated in FIG. 3 is used, the fluid-permeable liner 4 faces the patient and the fluid barrier 22 faces away from the patient. The absorbent pad 20 may be secured in place in the same way as described above with respect to the absorbent pad 2.

In various implementations absorbent pads 2 and 20 are configured to be used at or near a wound of a patient to absorb fluids discharging from the patient and/or to also be used as a hot or a cold compress. The fluids may therefore be biological fluids or "biofluids" as they are commonly known in the art, including any liquid originating from the body of a living person or animal such as, by non-limiting example, blood, urine, feces, water, saline (such as a saline irrigating solution that is used to flush and/or cleanse a patient's eye or other body portion), vaginal secretion, birthing fluids and so forth. The fluids may be biohazardous. The patient may be a human or an animal. A fluid discharge area may include, by non-limiting example: a bleeding or otherwise fluid-discharging wound, abscess, injury, scrape, cut, puncture, burn, bruise, laceration, gash, amputation or incision; vaginal discharges before, during, and/or after a vaginal or c-section birthing and/or during a menstruation; urinal discharges; fecal discharges; and the like. A fluid discharge area may also include an overspill area where all or some of the fluid is not originating from a patient such as, by non-limiting example, an area near an eye of the patient that is being flushed with irrigating saline solution, wherein the absorbent pad 2 or 20 is placed nearby to absorb the irrigating saline solution, or any other area of a patient's body where irrigating solution is used for flushing, irrigating or otherwise cleaning the area of the patient's body. A fluid discharge area may also include a location underneath a patient where an absorbent pad 2 or 20 is placed to absorb overspill of some irrigating or other fluid to prevent it from soiling a mattress or other item underneath the patient, or to similarly capture urination or feces from an incontinent patient.

A desired location of a patient, for instance for use of the absorbent pad 2 or 20 as a hot or cold compress, could include any of the fluid discharge areas described above, or any others, and could also include, by non-limiting example: a bruise; black eye; contusion; swelling; bone fracture; sprain, and the like. In FIG. 4 the fluid discharge area/desired location is shown on the torso of a human patient. In other implementations the fluid discharge area/desired location may be at or proximate any portion of the body of a human or non-human animal patient including the head and all limbs, extremities, torso, stomach, back, neck and the like. Accordingly, the absorbent pads 2 and 20 in particular implementations are flexible so as to conform to the contour of the portion of the patient's body where they are placed. In areas of the body with hair the absorbent pad 2 or absorbent pad 20 may be used with or without removing or reducing the hair at the fluid discharge area or other desired location of a patient.

In implementations an adhesive may be placed on the first side 6 to adhere the fluid-permeable liner 4 to the fluid discharge area or other desired location of the patient. This adhesive could be in the shape of a strip similar to the shape of the coupler 14 shown in the drawings and may include a removable portion to be used during pre-use storage and removed when it is desirable to adhere the fluid-permeable liner 4 to the discharge area.

In implementations the fluid-permeable liner 4 includes spunbond polypropylene supplied by ATEX, Inc. of Gainesville, Ga. and sold under the product name of AXAR Hydrophilic, and having a composition of polypropylene between about 94-98 weight percent, color pigment between about 2-6 weight percent, and mixture of nonionic emulsifiers and special antistatic agents of about 0.2-0.8 weight percent. In other implementations the fluid-permeable liner 4 may include any other fluid-permeable natural or synthetic material. In implementations the fluid-permeable liner 4 may also include an antimicrobial agent.

In implementations the absorbent material 12 includes one or more absorbents and/or one or more superabsorbents and/or one or more antimicrobial agents. In implementations the superabsorbent includes about 5% to 65% of the weight of the combination of absorbent(s), superabsorbent(s) and antimicrobial agent(s). In implementations the superabsorbent is a nonwoven superabsorbent. In implementations the antimicrobial agent(s) include about 0.005% to 1% of the total weight of the combination of absorbent(s), superabsorbent(s) and antimicrobial agent(s). In implementations the absorbent material 12 is configured such that the absorbent pad 2 or 20 is able to absorb up to thirty times its weight in fluid. In implementations the absorbent material 12 may be configured to absorb up to about 15 times its weight of 0.9% normal saline solution and up to about 30 times its weight of water.

In implementations the absorbent pads 2 and 20 may absorb up to ten times more than a conventional absorbent pad commonly known in the industry as a "chux" or "blue pad." In implementations an absorbent of the absorbent material 12 includes a matrix of Kraft fluff pulp and bonding fiber and the superabsorbent includes microscopic super absorbent polymer (SAP) beads and/or olefin/alkyl carboxylate co-polymer and/or an inorganic salt, each of which may be technical grade. In implementations the microscopic SAP beads are hydrophilic. In various implementations, additional chemicals may be included such as, by non-limiting example, zeolite, silver, zinc, iodine, copper, and ammonium.

In implementations the coupler 14 could include some other coupling mechanism other than hooks 16 such as, by non-limiting example: fibers, loops, an adhesive, and the like. In implementations the overwrap 18 may be an elastic bandage, ACE bandage, elastic wrap, compression bandage or crepe bandage or any other type of overwrap or dressing. The overwrap 18 may be tightened in order to increase pressure to a fluid discharge area or may be loosened to decrease pressure.

In implementations the absorbent pad 2 or 20 is configured such that fluid emanating from a fluid discharge area or fluid which is intentionally placed into the absorbent pad 2 or 20 at the surface of the fluid-permeable liner 4 moves away from the fluid-permeable liner 4 into the absorbent material 12 such that the fluid-permeable liner 4 remains dry to the touch during or shortly after use.

In implementations the absorbent material 12 includes an antimicrobial agent. In implementations the antimicrobial agent may include a silver ion antimicrobial agent supplied by AgION Technologies of Wakefield, Mass. including sodium aluminosilicate (zeolite), silver, zinc and ammonium and having the chemical formula $X_{2/n}O$—$Na_2O$—$Al_2O_3$—$2SiO_2$, where "X" is the cation of each of the previously listed chemicals. The zeolite may be zeolite A (CAS number 68989-22-0). Some or all of the antimicrobial agent may be included in the absorbed material in the form of about 1-2 micron particles. In implementations the antimicrobial agent is configured to inhibit microbial growth proximate the fluid discharge area or other desired location of a patient. Other antimicrobial agents that may be included may be those that contain iodine or copper ions.

The fluid barrier 22 is configured to disallow or discourage fluid from passing through it. The fluid barrier 22 may also have high coefficient of friction with a common floor surface, tabletop surface, stretcher or other material or surface such as to give it anti-slip properties. In implementations the fluid barrier 22 includes a polymeric film supplied by Pliant Corporation of Schaumburg, Ill. and includes one or more of the following: linear low density polyethylene (LDPE), medium density polyethylene (MDPE), high density polyethylene (HDPE), ethane, copolymer Polyolefin/Ethene, Octene-lHomopolymer, LLDPE, mLLDPE, or uLLDPE/LDPE.

In implementations the absorbent pad 2 or 20 is configured to assist in/and or facilitate the solidification of bio fluids emanating from a fluid discharge area of a patient such as, by non-limiting example, a jellification process by which water molecules of the bio fluid adhere to the surface of microscopic SAP beads in the absorbent material 12 and form a gel and the non-water remnant of the bio fluid then comprises solid particles.

Various implementations of absorbent pads 2 and 20 may be used in a method of using an absorbent pad 2 or 20 as a hot or cold compress. In such instances the absorbent material 12 is configured to retain a predetermined amount of liquid such as, by non-limiting example, water, and enable the retained liquid to be cooled or heated. The absorbent pad 2 or 20 may then be placed on or against a desired location of a patient's body and, although it already has absorbed some liquid, is capable of additionally absorb more liquid emanating from a fluid discharge area of a patient. Thus the absorbent pad 2 or 20 may function both as a hot or cold compress and simultaneously to absorb issuing fluids.

One implementation of a method of using an absorbent pad 2 or 20 as a compress may include absorbing a predetermined quantity of liquid into an absorbent pad 2 or 20 having a fluid-permeable liner 4 in a first side 6 of the absorbent pad 2 or 20, the absorbent pad 2 or 20 having an absorbent material 12 configured to absorb a maximum quantity of liquid greater than the predetermined quantity of liquid and further having a second side 8 substantially parallel with the first side 6. The predetermined quantity of liquid may be heated and/or cooled to a desired temperature and the absorbent pad 2 or 20 may be placed at a desired location of a patient. Liquid may be prevented from passing through the second side 8 of an absorbent pad 20 with a fluid barrier 22. The absorbent pad 2 or 20 may be secured to the desired location through the engagement of hooks 16 on the second side 8 with fibers in an overwrap 18 wrapped around the patient at the desired location.

A predetermined quantity of liquid may be heated to a desired temperature by microwaving the absorbent pad 2 or 20. The predetermined quantity of liquid may be cooled to a desired temperature by cooling the absorbent pad 2 or 20 in a refrigerator or freezer. The absorbent pad 2 or 20 may be adhered to the desired location of the patient with an adhesive. Microbial growth proximate the desired location may be inhibited through the use of an antimicrobial agent dispersed in the absorbent material 12. The predetermined quantity of liquid may be retained within the absorbent material 12 while additional liquid from a fluid discharge area of a patient is additionally absorbed into the absorbent material 12. The absorbent pad 2 or 20 may maintain a substantially dry surface at the fluid-permeable liner 4 after absorbing liquid from a fluid discharge area of a patient by drawing the liquid from the fluid discharge area of the patient into the absorbed material away from the fluid-permeable liner 4. The absorbent material 12 may absorb up to about 15 times its weight of 0.9% normal saline solution and up to about 30 times its weight of water. In various implementations of the method, the method may further include absorbing a quantity of fluid issuing from the patient.

Another implementation of the method may include absorbing a predetermined quantity of liquid into the absorbent material 12 of an absorbent pad 2 through a fluid-permeable liner 4 included in a first side 6 and in a second side 8 of the absorbent pad 2, the predetermined quantity of liquid being less than a maximum quantity of liquid absorbable by the absorbent material 12 and the fluid-permeable liner 4 at least partially surrounding the absorbent material 12; one of heating or cooling the liquid to a desired temperature; placing the first side 6 onto a desired location of a patient; and securing the absorbent pad 2 to the fluid discharge area by coupling an overwrap 18 to a second side 8 of the fluid-permeable liner 4, where the second side 8 is substantially parallel with the first side 6; and where coupling the overwrap 18 to the second side 8 includes causing loops of the overwrap 18 to engage with hooks 16 of the second side 8, thereby forming a hook-and-loop fastener. Method implementations may likewise include absorbing a quantity of fluid issuing from a patient.

Another method of using an absorbent pad 2 or 20 may include providing an absorbent pad 2 or 20 having a fluid-permeable liner 4 in a first side 6 of the absorbent pad 2 or 20 and a fluid barrier 22 in a second side 8 of the absorbent pad 2 or 20, the absorbent pad 2 or 20 having an absorbent material 12 configured to absorb a predetermined quantity of liquid, the predetermined quantity of liquid being less than a maximum quantity of liquid absorbable by the absorbent material 12; wherein the absorbent pad 2 or 20 is further configured to: allow heating and cooling of the predetermined quantity of liquid in the absorbent material 12 to a desired temperature; and allow the first side 6 of the absorbent pad 2 or 20 to contact a desired location of a patient. In implementations the predetermined quantity of liquid is one of 0.5 cups, 0.75 cups, 1 cup and 1.5 cups, In various method implementations the absorbent pad 2 or 20 may be heated and/or cooled in the following manner: preloading the absorbent pad 2 or 20 with fluid which may consist of warm tap water poured evenly over the absorbent pad 2 or 20; letting the absorbent pad 2 or 20 stand until water cannot be squeezed out (which may take about a minute in particular implementations), then heating the absorbent pad 2 or 20 in a microwave oven for about 1-2 minutes (for a hot absorbent pad 2 or 20) or placing the absorbent pad 2 or 20 in a freezer for about an hour and then microwaving it for about 30 seconds (for a cool absorbent pad 2 or 20). In implementations wherein the absorbent pad 2 or 20 has a size of about 3.5 inches by 12 inches the absorbent pad 2 or 20 may be preloaded with about 0.5 cup of water. Other pad sizes may have the following preload amounts: 4 inch by 14 inch-about 0.75 cups water; 5 inch by 16 inch-about 1 cup water; 6 inch by 18 inch-about 1.5 cups water; 9 inch by 9 inch-about 1 cup water.

In various implementations the absorbent pads 2 and 20 are configured to be microwaveable without being damaged, thus allowing heating of the predetermined amount of liquid by microwaving. However, other methods, such as heating the pad using a heated surface such as a hot plate may also be used.

In various implementations an absorbent pad 2 or 20 could be used together with a stick, such as a broom stick, or other pushing/pulling implementation or apparatus, to form a cleaning apparatus that could be used to clean a floor surface. The stick or other pushing/pulling apparatus may have loops or fibers or some other item to engage with the hooks 16 of the absorbent pad 2 or 20 to couple the two together when desired and to remove the two when desired, such as for cleaning or replacing of the absorbent pad 2 or 20. An example of such an absorbent pad implementation can be found in FIG. 2 and the corresponding disclosure of U.S. Provisional Patent Application 61/392,942, entitled "Dressing Systems, Fluid Management Systems, Hot/Cold Pack Systems and Related Methods" previously incorporated by reference.

In implementations the absorbent pads 2 and 20 may be used to absorb irrigation solution such as, by non-limiting example, saline solution used to flush a patient's eye or other body portion. In such an implementation the absorbent pad 2 or 20 may be placed below the patient such as on a bed or other item upon which the patient sits or lies. An absorbent pad 2 or 20 may be heated or cooled and placed underneath an animal such as a dog, as a warming pad after a surgery or at any other time when a warming pad is desired, or as a cooling pad for instance during transportation of an animal.

In places where the description above refers to particular implementations of absorbent pads and related methods, it should be readily apparent that a number of modifications may be made without departing from the spirit thereof and that these implementations may be applied to other absorbent pads and related methods.

The invention claimed is:

1. A method of using an absorbent pad, the method comprising:
absorbing a predetermined quantity of liquid into an absorbent pad comprising a fluid-permeable liner comprised in a first side of the absorbent pad, the fluid-permeable liner comprising an antimicrobial agent, and the absorbent pad comprising an absorbent material configured to absorb a maximum quantity of liquid greater than the predetermined quantity of liquid and further comprising a second side of the absorbent pad substantially parallel with the first side, the second side comprising a fluid barrier such that the absorbent pad is only liquid permeable through the first side, thus forming a cavity;
one of heating and cooling the predetermined quantity of liquid comprised in the absorbent material to a desired temperature;
abutting the first side of the absorbent pad to a desired location of a patient; and securing the absorbent pad to the desired location through the engagement of hooks comprised on the second side with fibers comprised in an overwrap wrapped around the patient at the desired location, wherein the overwrap is selectively decouplable from the absorbent pad through disengagement of the fibers from the hooks.

2. The method of claim 1, further comprising cooling the predetermined quantity of liquid to the desired temperature by placing the absorbent pad in one of a refrigerator and a freezer.

3. The method of claim 1, further comprising inhibiting microbial growth proximate the desired location with an antimicrobial agent dispersed in the absorbent material.

4. The method of claim 1, further comprising retaining the absorbed predetermined quantity of liquid within the absorbent pad while absorbing additional liquid from a fluid discharge area of the patient.

5. The method of claim 1, further comprising maintaining a substantially dry surface at the fluid-permeable liner after absorbing liquid from a fluid discharge area of a patient by drawing the liquid from the fluid discharge area of the patient into the absorbent material away from the fluid-permeable liner.

6. The method of claim 1, wherein absorbing a predetermined quantity of liquid further comprises wherein the absorbent material is configured to absorb up to about 30 times its weight of water.

7. The method of claim 1, further comprising heating the predetermined quantity of liquid to the desired temperature by microwaving the absorbent pad.

8. The method of claim 1, wherein the absorbent material is configured to absorb up to about 15 times its weight of 0.9% normal saline solution.

9. The method of claim 1, wherein the first side of the absorbent pad further comprises an adhesive to adhere the fluid-permeable liner to a fluid discharge area of the patient.

10. The method of claim 1, wherein the absorbent pad assists in converting a fluid discharged from the patient into a solid.

11. The method of claim 1, wherein the fluid-permeable liner comprises spunbond polypropylene.

12. The method of claim 11, wherein the fluid-permeable liner comprises between 94% and 98% of polypropylene by weight.

13. The method of claim 12, wherein the fluid-permeable liner comprises between 0.2% and 0.8% of a mixture of nonionic emulsifiers and special antistatic agents by weight.

14. The method of claim 1, wherein the absorbent material comprises superabsorbents and one or more of absorbents and antimicrobial agents, and wherein the superabsorbent comprises between about 5% and 65% of the total weight of the one or more of absorbents, superabsorbents, and antimicrobial agents.

15. The method of claim 1, wherein the absorbent material comprises a nonwoven superabsorbent.

16. The method of claim 1, wherein the absorbent material comprises a carboxylate co-polymer.

17. The method of claim 1, wherein the absorbent material comprises a matrix of kraft fluff pulp and bonding fiber.

18. The method of claim 1, wherein the second side of the absorbent pad comprises one or more of linear low density polyethylene, medium density polyethylene, and high density polyethylene.

19. The method of claim 1, wherein the overwrap comprises an elastic bandage.

20. A method of using an absorbent pad, the method comprising:
absorbing a predetermined quantity of liquid into an absorbent pad comprising a fluid-permeable liner comprised in a first side of the absorbent pad, the fluid-permeable liner comprising spunbond polypropylene, between 94% and 98% of polypropylene by weight, and between 0.2% and 0.8% of a mixture of nonionic emulsifiers and special antistatic agents by weight, and the absorbent pad comprising an absorbent material configured to absorb a maximum quantity of liquid greater than the predetermined quantity of liquid and further comprising a second side of the absorbent pad substantially parallel with the first side, the second side comprising a fluid barrier such that the absorbent pad is only liquid permeable through the first side, thus forming a cavity;
one of heating and cooling the predetermined quantity of liquid comprised in the absorbent material to a desired temperature;
abutting the first side of the absorbent pad to a desired location of a patient; and
securing the absorbent pad to the desired location through the engagement of hooks comprised on the second side with fibers comprised in an overwrap wrapped around the patient at the desired location, wherein the overwrap is selectively decouplable from the absorbent pad through disengagement of the fibers from the hooks.

21. A method of using an absorbent pad, the method comprising:
absorbing a predetermined quantity of liquid into an absorbent pad comprising a fluid-permeable liner comprised in a first side of the absorbent pad, the absorbent pad comprising an absorbent material comprising a matrix of kraft fluff pulp and bonding fiber, the absorbent material configured to absorb a maximum quantity of liquid greater than the predetermined quantity of liquid, and the absorbent pad further comprising a second side of the absorbent pad substantially parallel with the first side, the second side comprising a fluid barrier such that the absorbent pad is only liquid permeable through the first side, thus forming a cavity;
one of heating and cooling the predetermined quantity of liquid comprised in the absorbent material to a desired temperature;
abutting the first side of the absorbent pad to a desired location of a patient; and
securing the absorbent pad to the desired location through the engagement of hooks comprised on the second side with fibers comprised in an overwrap wrapped around the patient at the desired location, wherein the overwrap is selectively decouplable from the absorbent pad through disengagement of the fibers from the hooks.

* * * * *